United States Patent [19]

Byrne et al.

[11] Patent Number: 5,538,009
[45] Date of Patent: Jul. 23, 1996

[54] BIOPSY NEEDLE ASSEMBLY

[75] Inventors: John R. Byrne, Watertown, Wis.; Jan L. Como, Palatine, Ill.; Gregory D. Volan, Boulder, Colo.; Stephen Kuehn, Franklin, Wis.; Terrence W. Snyder, Chenango Forks, N.Y.; T. Michael Dennehey, Arlington Heights, Ill.; David A. Winchell, deceased, late of Fox Lake, Ill., by JoAnne Winchell, legal representative

[73] Assignee: Baxter International, Inc., Deerfield, Ill.

[21] Appl. No.: 278,413

[22] Filed: Jul. 21, 1994

[51] Int. Cl.⁶ .................................................. A61B 10/00
[52] U.S. Cl. .................................................. 128/754
[58] Field of Search ........................... 128/749, 751–753; 606/167, 170

[56] References Cited

U.S. PATENT DOCUMENTS

| | | | |
|---|---|---|---|
| 3,893,445 | 7/1975 | Hofsess . | |
| 4,262,676 | 4/1981 | Jamshidi | 128/754 |
| 4,266,555 | 5/1981 | Jamshidi | 128/753 |
| 4,469,109 | 9/1984 | Mehl | 128/753 |
| 4,630,616 | 12/1986 | Tretinyak | 128/753 |
| 4,793,363 | 12/1988 | Ausherman et al. | 128/754 |
| 4,838,282 | 6/1989 | Strasser et al. | 128/754 |
| 4,969,870 | 11/1990 | Kramer et al. | 604/51 |
| 4,994,036 | 2/1991 | Biscoping et al. | 604/158 |
| 5,078,695 | 1/1992 | Farrar, Jr. et al. | 604/192 |
| 5,106,376 | 4/1992 | Mononen et al. | 604/164 |
| 5,147,308 | 9/1992 | Singer | 604/117 |
| 5,151,086 | 9/1992 | Duh et al. | 604/51 |
| 5,257,632 | 11/1993 | Turkel et al. | 128/754 |
| 5,279,306 | 1/1994 | Mehl | 128/754 |
| 5,282,477 | 2/1994 | Bauer | 128/754 |
| 5,331,972 | 7/1994 | Wadhwani et al. | 128/754 |
| 5,385,151 | 1/1995 | Scarfone et al. | 128/754 |

*Primary Examiner*—Max Hindenburg
*Attorney, Agent, or Firm*—Allan O. Maki; Robert A. Stenzel

[57] ABSTRACT

A bone marrow biopsy needle assembly includes an elongated tubular cannula having an axially extending lumen therethrough, and a cannula handle attached to the proximal end of the cannula, the cannula handle extending transversely to the axis of the cannula and having a cavity aligned with and open to the proximal end of the cannula. The handle is provided with a cover connected to the cannula by means of a living hinge. A stylet having a knob affixed to its proximal end which knob is sized to fit within the cavity with the stylet slidably received within the cannula lumen. The cavity is provided with projections that engage the knob to prevent relative rotation between the stylet and the cannula. A guide is provided to facilitate insertion of a stylet into the cannula for sample removal.

11 Claims, 3 Drawing Sheets

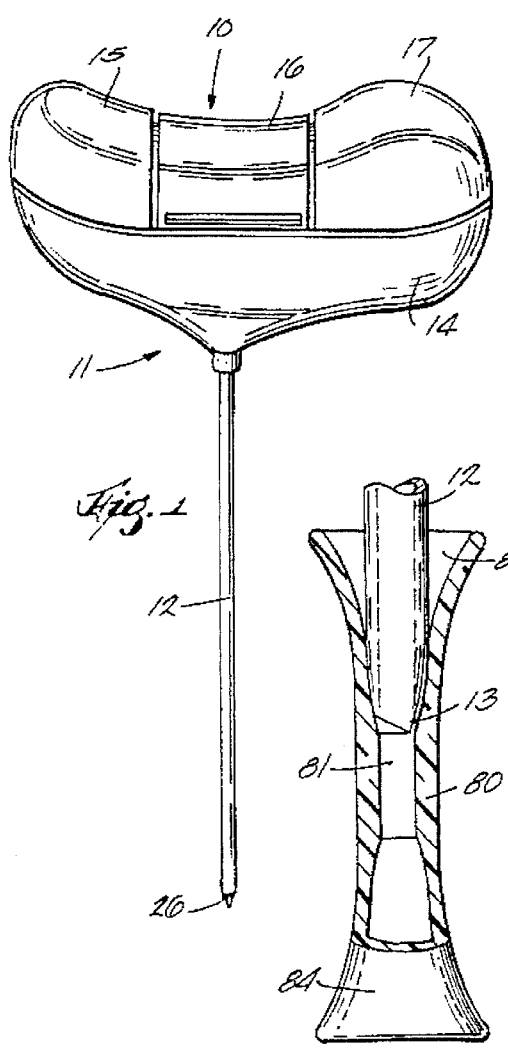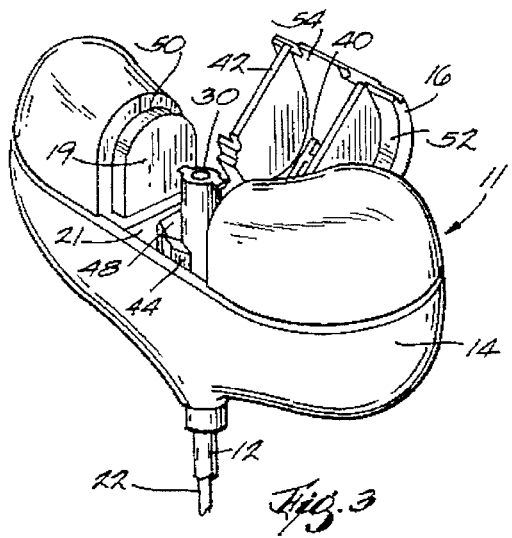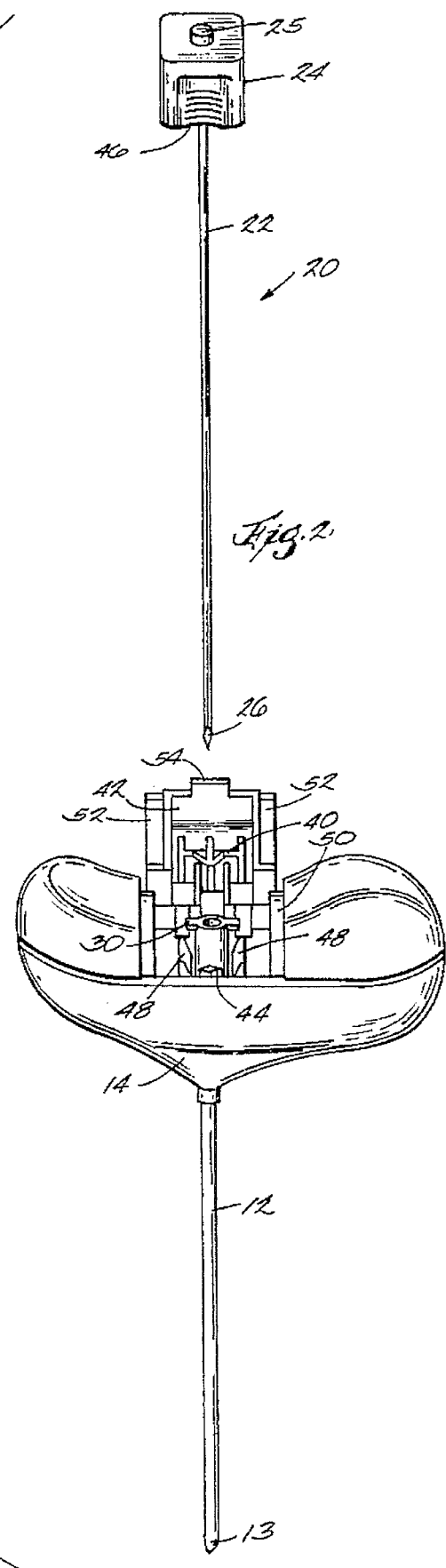

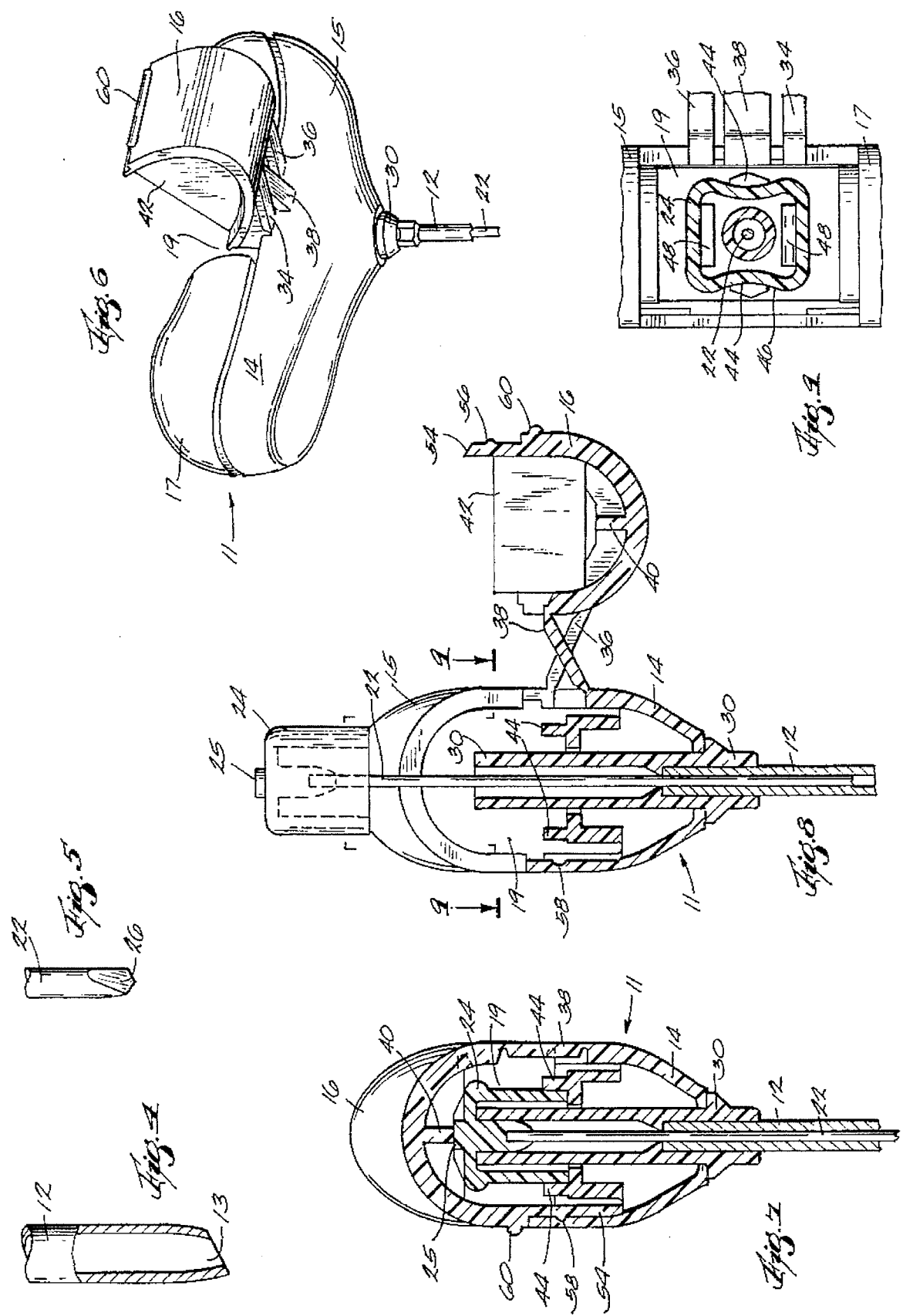

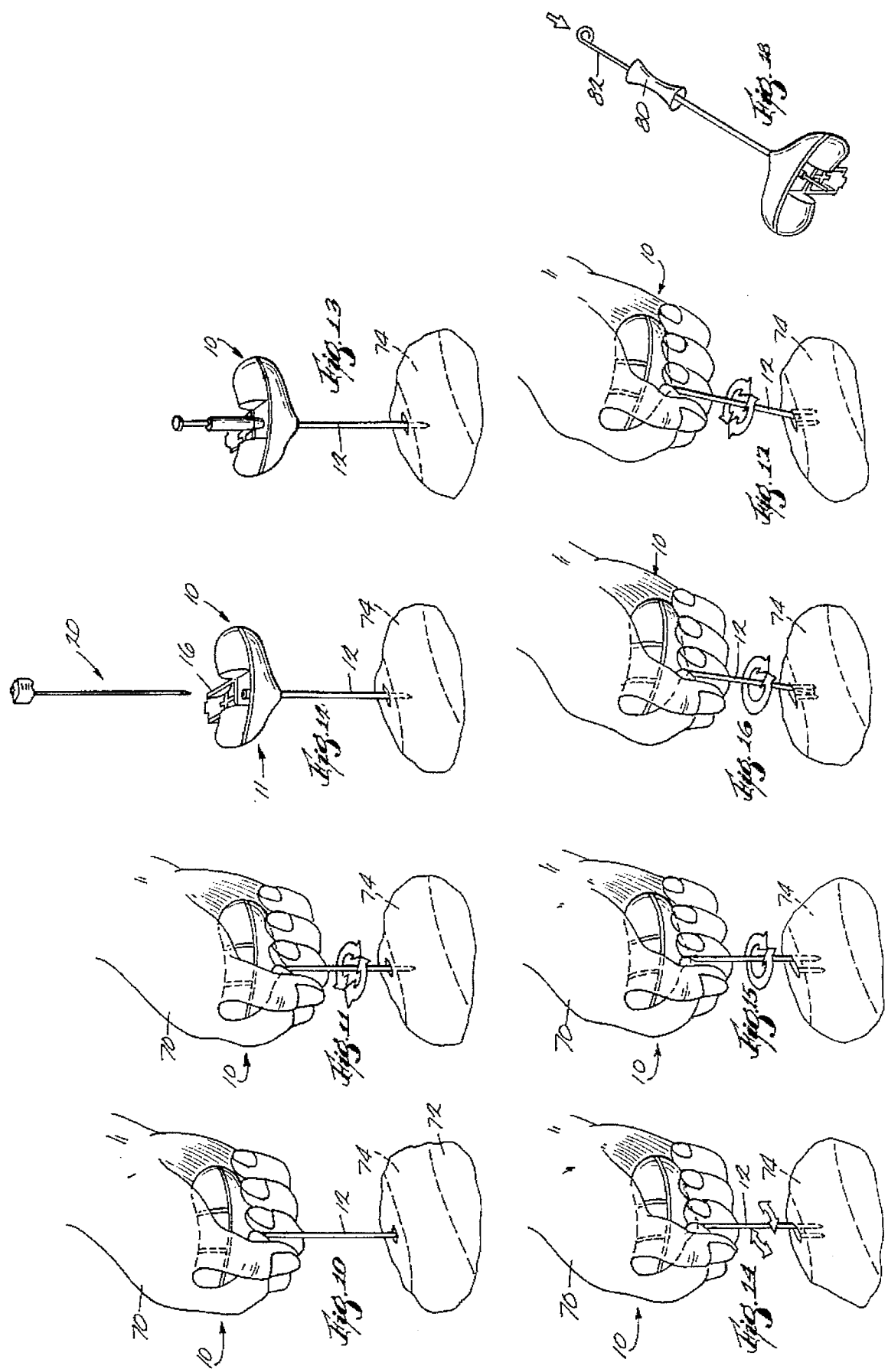

BIOPSY NEEDLE ASSEMBLY

TECHNICAL FIELD

The invention relates generally to the field of medical instruments, and more particularly to those instruments employed in biopsy, aspiration, and transplant procedures of bone marrow.

BACKGROUND OF THE INVENTION

It is frequently desirable to take biopsy samples from a patient. In bone marrow biopsy, it is always necessary to puncture the bone of a patient in order to retrieve bone marrow which normally exists only in the center of a bone.

It may be desirable to retrieve bone marrow for several different reasons. In one type of bone marrow procedure, it is desirable to retrieve a "core" of bone marrow to examine bone marrow architecture. This procedure may be useful in determining whether a patient has cancer and the extent of cancerous cells that may exist. Examining a bone marrow core typically involves an extended period of time in which the core is first prepared and then sliced into thin samples which are examined under a microscope.

In other bone marrow procedures, it is desirable to simply aspirate cells of the bone marrow to make a relatively rapid examination to indicate the state of a patient's disease and to aid in the diagnosis of a patient.

Finally, in other bone marrow procedures, multiple aspirations of bone marrow are conducted to perform a bone marrow transplant. While each of these procedures has different goals, they all require that the bone be punctured in order to access the bone marrow within. Thus, it is important to provide a needle which enhances the ability of the user to puncture bone with minimal trauma to the patient.

All bone marrow biopsy, aspiration and transplant needles currently on the market have a handle with a cannula extending outwardly from the handle. The handle is used by the doctor to apply force to the cannula as the cannula penetrates the bone. Such needles typically include a stylet with a sharpened tip which is inserted through the cannula and is used to initially penetrate the bone. The stylet also serves to occlude the cannula while the bone is penetrated, so that the marrow sample subsequently taken is free from bone chips. The stylet is then removed and bone marrow is withdrawn from the patient by manipulating the cannula to cause bone marrow to move into the interior of the cannula. In some cases a slight suction is applied to the cannula to hold the bone marrow specimen within the cannula as the device is removed from the patient.

Bone marrow needles have traditionally been designed so that the needle is attached to the center of the handle. While many physicians feel comfortable with a centrally attached needle, it has now been discovered that it may be easier to guide a needle with a user's index finger when the needle is not centrally located on the handle of the needle assembly. It has also recently been discovered that when an off-center device is used, it is important to insure that a physician's arm, wrist, and index finger are all generally in alignment with the cannula of the needle to provide enhanced control over the needle. Examples of such devices are described in U.S. Pat. Nos. 4,469,109 and 4,838,282.

A disadvantage of most bone marrow needle assemblies currently on the market is that when the stylet is removed from the cannula, the shape of the handle typically is materially changed. For example, the bone marrow needle assembly described in U.S. Pat. No. 4,838,282 involves removing approximately half of the handle assembly when the stylet is removed from the cannula. It has recently been discovered, as part of the subject invention, that it is desirable to maintain the original shape of the handle after the stylet has been removed to allow a physician to more easily manipulate the cannula within a patient's bone.

OBJECTS OF THE INVENTION

It is an object of the invention to provide a bone marrow needle assembly having an ergonomically shaped offset handle to assist a physician in inserting a needle into a patient.

It is still another object of the invention to provide a bone marrow needle assembly having a handle design such that the shape of the handle remains essentially the same after the stylet has been removed. In accordance with a related aspect of the invention, the stylet is provided with a handle that is received within a gap or hollow portion in the cannula handle. A hinged cover provides access to the hollow portion for placement and removal of the stylet. It is a further object to provide such an assembly wherein an improved means is provided to prevent rotation of the stylet relative to the cannula.

SUMMARY OF THE INVENTION

In a preferred embodiment of the invention the handle has a proximal surface which has a somewhat saddle shaped offset surface which, when grasped by a physician, conforms to the shape of the physician's palm. The off-center radius causes the handle to have a first relatively narrow end and a second relatively wide end. The handle also has a curved lower surface designed to be easily gripped by a user's fingers. In the preferred embodiment, the proximal end of the cannula is connected to the lower surface of the handle toward the relatively narrow end. Thus, when a user grips the handle, the user's index finger can be naturally applied to the cannula to guide the cannula into a patient. The cannula handle is connected to the cannula at an oblique angle that places the user's wrist and forearm in general alignment with the user's index finger and the axis of the cannula.

Briefly summarized, the invention provides a bone biopsy needle assembly which includes an elongated tubular cannula having an axially extending lumen therethrough, and a cannula handle attached to the proximal end of the cannula. Each lateral end of the cannula handle extends transversely to the axis of the cannula at an oblique angle and has a cavity aligned with and open to the proximal end of the cannula. The handle is provided with a cover preferably connected to the cannula by means of a living hinge. A stylet having a knob affixed to its proximal end, which knob is sized to fit within the cannula handle cavity with the stylet slidably received within the cannula lumen. The cavity is provided with projections that engage the knob to prevent relative rotation between the stylet and the cannula.

BRIEF DESCRIPTION OF THE DRAWINGS

FIG. 1 is a side elevational view of the biopsy needle assembly of this invention;

FIG. 2 is a perspective view of a biopsy needle assembly of this invention with the stylet withdrawn from the cannula;

FIG. 3 is a fragmentary perspective view of the cannula handle component of the system with the cover in the open position to expose the proximal cannula assembly;

FIG. 4 is a fragmentary enlarged view of the cannula tip with parts shown in cross-section;

FIG. 5 is a side elevational expanded fragmentary view of a stylet tip;

FIG. 6 is a perspective rear view of the cannula handle with cavity cover in the open position to show the hinge detail;

FIG. 7 is a fragmentary cross-sectional view of the handle with stylet in place shown in the closed position;

FIG. 8 is a view of the handle of FIG. 7 with the cover shown in the open position and with the stylet partially withdrawn from the cannula;

FIG. 9 is a fragmentary cross-sectional view taken along line 9—9 of FIG. 8;

FIG. 10 is a fragmentary perspective view illustrating the manner in which the device of this invention is grasped and illustrating the initial entry into a body;

FIG. 11 shows a view of the device of FIG. 10 as it is penetrating a bone;

FIG. 12 is a view of the device of FIG. 10 after the marrow cavity of the bone has been entered and showing the withdrawal of the stylet;

FIG. 13 shows the device of FIG. 10 during aspiration of material utilizing a syringe;

FIGS. 14—17 illustrate the use of the device of FIG. 10 to reenter the bone cavity to obtain a biopsy specimen;

FIG. 18 illustrates the use of a probe guide and probe to remove a biopsy specimen from the cannula; and FIG. 19 is a side view of the probe guide and fragmentary cannula tip with parts broken away and in section.

DETAILED DESCRIPTION OF A PREFERRED EMBODIMENT

Referring more particularly to the drawings there is seen a biopsy needle assembly 10 which includes a hollow cannula 12 having an open, sharpened distal end 13, and being attached to a handle 11 at its proximal end. Handle 11 is provided with a cover 16 that pivots open to the position seen in FIGS. 2 and 3 to expose a gap or hollow portion 19 of the handle into which the cannula hub 30, which is secured to the proximal end of cannula 12, is open. Ends 15 and 17 of handle 14 extend laterally and have central axes that are attached to cannula 12 at an oblique angle with respect to the cannula axis so as to form a saddle shaped configuration that will conform to the hand of a user. End 15 which is designed to be grasped by the forefinger and thumb of the user is of a smaller cross-section and shorter than end 17 which is designed to engage the user's palm.

Handle 11 is formed from a bottom portion 14, which includes cover 16 which is hinged to the bottom portion 14. Upper lateral end portions of the handle 15 and 17 are preferably formed from a single molded piece connected together by means of a flat connecting portion 21 that forms a bottom to hollow portion 19 of the handle assembly. The handle can, thus, conveniently be formed from two molded parts. A hollow tubular cannula hub 30 is molded to the proximal end of cannula 12 and serves to secure the cannula 12 to handle 11 by tight frictional engagement of hub 30 in an aperture through the distal surface of bottom 14 of the handle 11. Hub 30 extends upwardly into hollow portion 19. The hollow interior of cannula hub 30 is connected in fluid flow communication with the hollow interior of cannula 12 as can best be seen in FIGS. 7 and 8. Cannula hub 30, as well as any other parts coming into fluid contact, are preferably formed from a polystyrene terpolymer of acrylonitrile, butadiene and styrene (ABS) or, alternatively, a polycarbonate polymer.

A stylet having a shaft 22 and a handle 24 fits within the handle 11 with the distal end 26 of the stylet extending beyond the distal end 13 of cannula 12. Knob 24 is provided with a proximal projection 25 in order to provide additional compression resistance to the knob and to provide a surface against which internal ribs 40 of the handle are supported during use of the instrument.

Cover portion 16 is hingedly connected to the bottom part 14 of handle 11 by means of living hinges 34, 36 and 38. In the preferred configuration of these hinges best seen in FIGS. 6 and 8, it will be noted that the outermost hinges 34 and 36 are pivoted at a higher point on the base portion 14 of the handle than is the inner hinge 38. The upper end of central living hinge 38 is also hinged nearer the perimeter of cover 16. This causes rotational pivoting of cover 16 as it is opened, causing it to pivot out of the way of knob 14 more rapidly than would otherwise be the case. This hinge arrangement also holds the cover in a relatively elevated position as seen in FIG. 8 when open.

The handle components 14, 15, 16 and 17 are all preferably provided with ribs 40 to provide structural integrity and light weight to the handle 11. These components are all preferably formed from a polyolefin such as a high density polyethylene, polypropylene, or a polyester or similar thermoplastic polymeric material. The cover 16 is preferably provided with end walls 42 that provide a chamber surrounding knob 24 when the cover is in the closed position. Walls 42 thus provide a degree of resistance to rotation of the knob 24, preventing relative rotation between stylet 22 and cannula 12.

The base portion 21 is provided with upwardly extending projections 44 and 48. Projections 44 on the forward and rearward sides of the handle closely engage curved indentations 46 in the lower part of knob 24. Knob 24 also fits tightly over the outside of projections 48, thus forming a structure that prevents relative rotation of stylet 22 and cannula 12 even when substantial force is applied to the needle assembly by the physician.

Lip 54 of cover 16 fits within the bottom part of handle 14 as can be seen in FIG. 7. An indentation 58 is provided in lower handle portion 14 to matingly receive a projection 56 of the cover in order to retain the cover in a closed position. A ridge 60 is provided to form a surface to be grasped in order to open cover 16.

The procedure for use of the instrument of this invention is shown in FIGS. 10–19. As seen in FIG. 10, the needle, grasped in physician's hand 70, is introduced through an incision, through soft tissue 72 toward and into contact with bone structure 74, usually the posterior iliac spine. The needle is advanced into the marrow cavity by alternating 45 clockwise/counter-clockwise rotation. The cover 16 is then opened as seen in FIG. 12 and the stylet removed from the cannula. For sample aspiration syringe 76 is then attached to the cannula hub 30, which is preferably provided with a luer fitting for that purpose. Negative pressure is applied by quickly withdrawing the syringe plunger to remove an aspirated specimen.

The biopsy procedure is illustrated in FIGS. 15–19, wherein another penetration to the marrow cavity is made, and after removal of the stylet, the cannula is advanced into the marrow cavity to obtain a specimen. Optionally, a knob (not shown) similar to the stylet knob 24 is included with the needle assembly and is placed in the handle to fill the space provided for knob 24. The specimen is detached from surrounding tissue by redirection and rotation of the cannula a number of times in each direction. The specimen is removed from the cannula as shown in FIG. 19 by introducing a probe 82 through the distal end of the cannula utilizing the probe guide 80 to insure easy insertion of the probe into the lumen of the cannula. The biopsy specimen is then pushed up into the proximal end of the cannula and through the cannula hub.

As seen, probe guide 80 is preferably a molded plastic shape in the form of a generally hourglass configuration. A cylindrical opening extends through the length of said elongated dimension of the guide between its ends. The cylindrical elongated opening has a diameter substantially equal to that of said interior lumen of cannula 12. Preferably there is at each end of the opening a flared outward enlargement for alignment with the distal end of the cannula and for forming a guide for insertion of a probe into said distal end of the cannula for removal of a biopsy specimen.

What is claimed is:

1. A bone biopsy needle assembly comprising:

an elongated tubular cannula having an axially extending lumen therethrough and having distal and proximal ends;

a cannula handle attached to the proximal end of said cannula, said cannula handle extending transversely to the axis of said cannula and having a cavity aligned with and open to the proximal end of said cannula, said handle having hinged thereto a cover providing access to said cavity, an orifice in said cavity in fluid flow communication with said cannula lumen, said orifice being coaxial with said cannula lumen, a stylet having a knob affixed to its proximal end, said knob being sized to fit within said cavity, an elongated stylet shaft extending from said knob slidably received within said cannula lumen, said stylet having a sharpened distal tip which extends distally from the distal end of said cannula, said cannula having a sharpened beveled distal end, said cavity retaining said knob so that force may be rotatably applied around either axis direction of said elongated stylet positioned in said cavity without relative rotation between said elongated stylet and said elongated cannula.

2. A needle assembly according to claim 1 wherein said cover is connected to said cannula handle by means of a living hinge.

3. An assembly according to claim 1 wherein said orifice is contained in a cannula hub molded to the proximal end of said cannula.

4. An assembly according to claim 3 wherein said cannula is secured to said handle by tight frictional engagement of said cannula hub in an aperture through the distal surface of said handle.

5. An assembly according to claim 4 wherein said living hinge comprises at least two segments of material connecting said cover to said handle, said segments each being attached to said handle and said cover at different elevations.

6. An assembly according to claim 4 wherein said handle comprise a distal component and a proximal component separate from, but connected to said distal component and said cover is formed integrally with said distal component.

7. An assembly according to claim 6 wherein said proximal portion is formed all of one piece comprising two opposed lateral ends forming the proximal part of said handle connected by a central portion fitting within said cavity that interconnects said lateral ends.

8. An assembly according to claim 7 wherein said central portion has an aperture to receive the cannula hub and proximally extending projections that are adapted to engage the handle of said stylet.

9. A bone biopsy needle assembly comprising:

an elongated tubular cannula having an axially extending lumen therethrough and having distal and proximal ends;

a cannula handle attached to the proximal end of said cannula, said cannula handle extending transversely to the axis of said cannula and having a cavity aligned with and open to the proximal end of said cannula, said handle having connected thereto, by means of a living hinge, a cover providing access to said cavity, a stylet having a knob affixed to its proximal end, said knob being sized to fit within said cavity, said stylet having a shaft adapted to fit within said cannula lumen and having a sharpened distal end extending distally beyond the distal end of said cannula, said cavity having projections for engaging and retaining said knob so that force may be rotatably applied around either axis direction of said elongated stylet positioned in said cavity without relative rotation between said elongated stylet and said elongated cannula, said stylet being removable from said cavity when said cover is open.

10. An assembly according to claim 9 wherein a cannula hub is affixed to the proximal end of said cannula, said hub being provided with an opening coaxial with and in fluid flow communication with said cannula lumen.

11. An assembly according to claim 10 wherein said cannula is secured to said handle by tight frictional engagement of said cannula hub in an aperture through the distal surface of said handle.

* * * * *